United States Patent [19]

Kobayashi et al.

[11] Patent Number: 4,744,830

[45] Date of Patent: May 17, 1988

[54] FIBROUS BINDER AND A METHOD FOR THE PREPARATION THEREOF

[75] Inventors: Yoshinari Kobayashi; Ryukichi Matsuo, both of Takamatsu, Japan

[73] Assignee: Agency of Industrial Science & Technology, Tokyo, Japan

[21] Appl. No.: 935,203

[22] Filed: Nov. 26, 1986

[30] Foreign Application Priority Data

Dec. 7, 1985 [JP] Japan .................. 60-275678

[51] Int. Cl.$^4$ .............................................. C08L 5/00
[52] U.S. Cl. .................................. 106/205; 106/208; 264/186
[58] Field of Search ................ 106/205, 208; 264/186

[56] References Cited

U.S. PATENT DOCUMENTS 3,503,769  3/1970  McDowell ................ 106/208
4,562,110  12/1985  Tong ........................ 264/186

*Primary Examiner*—Theodore Morris

*Attorney, Agent, or Firm*—Hopgood, Calimafde, Kalil, Blaustein & Judlowe

[57] ABSTRACT

The invention provides a fibrous binder capable of exhibiting a bonding ability in a dry condition for fibers having no self-adhesiveness in paper making but capable of imparting the paper made by use of the same with disintegrability into discrete fibers in a wet condition so that the paper is disposable in water. The fibrous binder is prepared by wet-spinning of an aqueous dope containing a water-soluble salt, e.g. sodium salt, of alginic acid and an alkyleneglycol ester of alginic acid in a specified proportion into a coagulation bath containing a water-soluble salt of certain metals, e.g. calcium, of which the ions are replaceable with the sodium ions of the water-soluble salt of alginic acid to convert the acid into a water-insoluble salt so as to form a water-insoluble gel in a fibrous form of a blend composed of the water-insoluble metal salt of alginic acid and the alkyleneglycol ester of alginic acid.

6 Claims, 1 Drawing Sheet

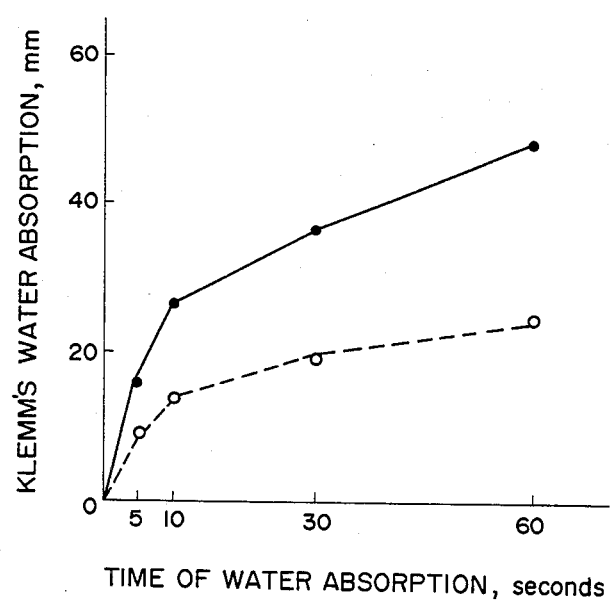

FIBROUS BINDER AND A METHOD FOR THE PREPARATION THEREOF

BACKGROUND OF THE INVENTION

The present invention relates to a fibrous binder capable of exhibiting fiber-to-fiber bonding when it is in a dry condition while the bonding ability is lost when it is converted into a hydrogel in water as well as a method for the preparation of such a fibrous binder.

As is well known, certain fibers or staples which cannot be made into paper as themselves due to the absence of self-adhesiveness or very poor self-adhesiveness thereof can be used in paper making when a water suspension thereof for paper making is admixed with a so-called fibrous binder such as fibers of polyvinyl alcohols, copolymers of ethylene and vinyl acetate, polyethylenes and polypropylenes as well as composite fibers thereof. Such a fibrous binder is used by admixing with the water suspension of the principal fibrous material for paper making and, when the sheet-like wet web of the fibers formed from the suspension is heated after drying, the fibrous binder is at least partly melted to exhibit bonding ability for the principal fibers or staples having no or little self-adhesiveness by themselves.

As a recent trend in the paper-making industry, the production is rapidly increasing of the paper products which can be rapidly disintegrated into a discrete fibrous form when put into water after use along with the increasing consumption of toilet paper and sanitary absorbent material disposable in water. The production of such water-disintegrable paper products may make a potential application of fibrous binders when the paper made by use thereof can readily be disintegrated in water.

Although various kinds of fibrous binders are known in the conventional paper-making industry as is mentioned above, none of them is suitable for use in the paper making of water-disintegrable paper products. For example, the fibrous binders made of a copolymer of ethylene and vinyl acetate, polyethylene or polypropylene are inherently very stable against and insoluble in water so that the paper made by use of such a fibrous binder can hardly be disintegrated in water into a discrete fibrous form. The fibrous binder made of a polyvinyl alcohol is also not soluble in water to be only swollen at room temperature so that the paper made by use of such a polyvinyl alcohol-made fibrous binder can be disintegrated only by a specific and troublesome treatment such as heating, addition of a chemical reagent and application of a large shearing force using, for example, a pulper machine. Accordingly, it is eagerly desired to develop a fibrous binder which can be used in making of paper rapidly disintegrable in water even under a relatively small shearing force as is given, for example, in a water flush of flush toilets.

SUMMARY OF THE INVENTION

An object of the present invention is therefore to provide a fibrous binder having a bonding ability for fibers in a dry condition to exhibit a reinforcing effect on the strength of paper but losing the bonding ability when it is converted into a hydrogel by absorbing water so that the paper made by use thereof can be readily disintegrated in water into a discrete fibrous form even under a relatively small shearing force.

Another object of the invention is to provide a method for the preparation of the above mentioned novel fibrous binder.

Thus, the fibrous binder of the present invention is a fibrous material formed of a water-insoluble gel of a mixture comprising a salt of alginic acid and an alkyleneglycol ester of alginic acid.

The above mentioned fibrous binder can be prepared by a method which comprises:

(a) dissolving a water-soluble salt of alginic acid and an alkyleneglycol ester of alginic acid in water to give an aqueous dope;

(b) wet-spinning the aqueous dope to form a fiber of a water-insoluble gel; and (c) drying the thus formed fiber of the water-insoluble gel.

BRIEF DESCRIPTION OF THE DRAWING

The FIGURE is a graph showing the Klemm's water absorption in mm of a rayon paper and a filter paper made by use of the fibrous binder of the invention as a function of the time of water absorption in seconds.

DETAILED DESCRIPTION OF THE PREFERRED EMBODIMENTS

As is described in the above given summary, the aqueous dope, from which the inventive fibrous binder is wet-spun, is prepared by dissolving a water-soluble salt of alginic acid and an alkyleneglycol ester of alginic acid. The water-soluble salt of alginic acid includes ammonium salt and salts of alginic acid with various metals such as sodium, potassium, magnesium, mercury and the like, of which sodium is preferred. These water-soluble salts can be used either singly or as a combination of two kinds or more according to need.

The other essential ingredient in the aqueous dope is an ester of alginic acid with an alkylene glycol such as ethyleneglycol, propyleneglycol, butyleneglycol and the like, of which propyleneglycol is preferred. They can be used either singly or as a combination of two kinds or more according to need. These esters can be prepared, for example, by the reaction of alginic acid and an alkylene oxide.

The aqueous dope should contain the alginic acid salt and the alkyleneglycol ester of alginic acid in a specified proportion in the range from 95:5 to 10:90 by weight. The fibrous binder prepared from the dope may be more readily converted into a hydrogel when the weight proportion of the alginic acid ester in the dope is larger though with sacrifice in respect of the velocity of coagulation in spinning to cause decrease in the working efficiency. This is the reason for the upper limit of 90% by weight in the proportion of the alginic acid ester.

The overall concentration of the water-soluble alginic acid salt and the alkyleneglycol ester of alginic acid in the aqueous dope should be in the range from 0.1 to 10% by weight. In the preparation of the aqueous dope, the salt and the ester each may be separately weighed and added to water to be dissolved therein. An alternative method is to prepare an alginic acid ester of a low degree of esterification in the esterification reaction of alginic acid with an alkylene oxide followed by conversion of the residual carboxyl groups into the form of a metal salt to give a material something like a so-called block copolymer provided that the proportion of the monomeric units of the alginic acid in the forms of salt and ester is in the above specified preferable range.

The aqueous dope prepared in the above described manner is then filtered to remove any water-insoluble matter and freed from bubbles before it is used for spinning. Spinning of the dope is performed by extruding the dope out of a spinnerette having a large number of spinning nozzles under pressurization, for example, with a gear pump into a coagulation bath. The coagulation bath is an aqueous solution containing a water-soluble salt of a metal which can be replaceable with the metallic ions in the metal salt of alginic acid so as to convert the alginic acid into a salt insoluble in water. The water-soluble salts dissolved in the coagulation bath include chlorides, sulfates, nitrates and phosphates of metals such as calcium, barium, strontium, aluminum, zinc, nickel, cobalt, chromium, copper, manganese, lead and the like, of which calcium is preferred. These water-soluble salts can be used either singly or as a combination of two kinds or more according to need. The coagulation bath should contain the water-soluble metal salt or salts preferably in a concentration of 0.05 to 10% by weight and may further contain water-soluble organic and/or inorganic acids.

The coagulation bath may optionally contain some other additives with an object to modify the surface properties of the fibrous binder prepared by spinning thereinto including, for example, hydrophilic organic solvents, e.g. methyl alcohol, ethyl alcohol, acetone, ethyl acetate, ethyl formate, acetamide and formamide, and various kinds of surface active agents.

Spinning of the aqueous dope into a fibrous form is performed in a wet process by extruding the dope through the nozzles of a spinnerette into the above described coagulation bath. The spinning nozzles should have a diameter preferably in the range from 0.01 to 0.5 mm. Although spinning nozzles having a smaller diameter may give fibers of higher fineness which may be advantageous in respect of the increased specific surface area, the nozzle diameter should be limited within the above mentioned range because fibers of unduly high fineness may be impractical in respect of the fiber strength. The fibrous binder of the invention should have a fineness, preferably, in the range from 0.1 to 1.0 denier as dried.

The fibers formed in the coagulation bath are wound around a godet and then chopped into staples having a length suitable for paper making in the range from 1.0 to 20.0 mm or, preferably, from 2.0 to 10.0 mm followed by drying.

The fibrous binder prepared in the above described manner retains the fibrous form when it is converted into a hydrogel in the presence of water so that the fibrous binder may be added to a water suspension of other stapled fibers or an aqueous suspension of a cellulosic pulp to aid paper making therefrom. When the wet sheet of paper laid on the paper-making screen from the suspension is dried, the fibrous binder serves to bond the fibers together into paper having sufficient strength. When such paper is brought into water, the fibrous binder bonding the fibers of paper is reversibly converted into a hydrogel which is no longer effective to bond the fibers so that the paper is readily disintegrated into discrete fibers.

The inventive fibrous binder is useful when a fibrous material having no self-adhesiveness is to be made into water-disintegrable paper by admixing the water suspension of the fibers with the inventive fibrous binder. Particularly suitable fibrous materials for water-disintegrable paper by use of the inventive fibrous binder include fibers of fluff pulp, rayon, cupra, chitin, collagen, acrylic polymers, polyolefins, polyamides, polyesters and the like. These fibrous materials are used in paper making sometimes in combination of two kinds or more. No paper can be made of these fibrous materials by themselves due to the lack of self-adhesiveness while water-disintegrable paper products can readily be manufactured in a conventional paper making process when the water suspension containing these fibrous materials is admixed with the inventive fibrous binder in an amount in the range from 10 to 100% by weight based on the amount of the fibrous material.

The fibers of the inventive fibrous binder are composed of a water-insoluble alginic acid salt and an alkyleneglycol ester of alginic acid while each of these constituents has no problem on the human health when the metallic constituents in the starting metal salt of alginic acid and the coagulation bath have no toxicity. Namely, they are approved as a food additive and are safe when human skin is contacted with these materials. In addition, they have an activity of hemostasis and other desirable pharmacological activities. Accordingly, the water-disintegrable paper products prepared using the inventive fibrous binder are free from regulations in any applications including the use as a food wrapping material. The paper has a high strength when it is in a dry condition while the paper is imparted with disintegrability into discrete fibers when it is put into water because the fibrous binder which has been in service of bonding the fibers together in the dry condition is converted into a hydrogel having no bonding ability by absorbing water. The disintegrability of the thus water-soaked paper is so high that the paper can readily be disintegrated into discrete fibers even under a relatively small shearing force as is given in the water flush in a flush toilet. Moreover, the paper is disintegrable in water having alkalinity because the fibrous binder in a water-swellable but water-insoluble form may be rapidly solubilized in an aqueous alkaline solution by the ion change of the metallic ions therein with the alkali metal ions in the solution.

In the following, a more detailed description is given of the inventive fibrous binder and the method for the preparation thereof by way of examples.

EXAMPLE 1

An aqueous dope for spinning was prepared by dissolving equal amounts of sodium alginate and a propyleneglycol ester of alginic acid in water in an overall concentration of 5% by weight based on water followed by filtration of the solution through a ceramic filter having an average pore diameter of 50 $\mu$m under pressurization of 3.5 kg/cm$^2$G to remove water-insoluble matters. The dope transferred into the dope tank of a wet-spinning machine was deaerated and freed from bubbles by keeping under a reduced pressure of $-760$ mmHg relative to the atmospheric pressure for 24 hours by suction with an aspirator. Thereafter, the dope tank was pressurized up to a pressure of 1.0 kg/cm$^2$G and the dope was extruded out of a platinum-made spinnerette having 1000 round holes of 0.01 mm diameter at a rate of 1.68 ml/minute controlled by use of a gear pump into a coagulation bath which was a 5% by weight aqueous solution of calcium chloride. The extruded dope was converted continuously into gel-like water-insoluble filaments. The filaments were passed through three sets of godets each composed of three so as to be slightly stretched by 1.3 times under tension by controlling the rotating velocity of the first set of godets at 20 rpm and the third set of godets at 26 rpm before winding on the last godet.

The filaments of continuous length thus obtained were very flexible having an agar-like appearance. The filaments having a fineness of about 0.5 denier as dried were cut and removed from the godets followed by dehydration on a centrifugal dehydrator and then chopped through a guillotine cutter into staples in a length of 3.0 mm to serve as a fibrous binder.

When put into water, the fibrous binder thus prepared was readily dispersed in water to have an appearance that the staples were seemingly dissolved in water. The aqueous suspension, however, had no stickiness since the fibrous binder was in a condition of fibrous hydrogel dispersed therein.

EXAMPLE 2

The fibrous binder prepared in Example 1, which was a fibrous material formed of a 50:50 by weight blend of a calcium alginate and propyleneglycol ester of alginic acid, alone was subjected to the paper making test according to the procedure specified in JIS P 8209. The wet sheet of the staples of the fibrous binder laid on the paper-making screen was taken up by transferring on to a sheet of filter paper and dried as such on the filter paper. The adhesion between the thus dried sheet of the fibrous binder and the filter paper was very firm with no possibility of peeling indicating that the fibers had made a very strong bonding with the fibers of natural cellulose to satisfy a requirement for a fibrous binder.

When the composite sheet of the fibrous binder and the filter paper was fully moistened with water, the wet sheet of the fibrous binder could readily be peeled off and separated from the filter paper leading to a conclusion that the bonding ability of the fibrous binder sheet was rapidly lost when it is in a wet condition.

EXAMPLE 3

Rayon paper was prepared according to the procedure specified in JIS P 8209 from a water suspension of staple fibers of rayon for paper making having a fineness of 1.5 denier and a fiber length of 5.0 mm and the fibrous binder prepared in Example 1 in an amount of 30 parts by weight per 70 parts by weight of the rayon fibers. The dispersibility of the fibers in water was very good and the paper had a quite satisfactory formation. The fibers of the fibrous binder were freed from the gel-like stickiness in the drying process so that the rayon paper had no tackiness differently from conventional rayon paper products made by use of a super-absorbent fibrous binder of the prior art. The rayon paper had a basis weight of 67.7 g/m$^2$, thickness of 0.26 mm, density of 0.258 g/cm$^3$ and breaking length of 1.89 km.

The FIGURE in the accompanying drawing is a graph showing the Klemm's water absorption of this rayon paper and a sheet of filter paper having a density of 0.5287 g/cm$^3$ by the solid-line curve and broken-line curve, respectively, determined according to the procedure specified in JIS P 8141 as a function of the time of water absorption. As is clear from this FIGURE, the rayon paper was excellently water-absorptive, especially, at the early stage of water absorption.

When the rayon paper was immersed in water for a while and vigorously agitated with a glass rod, the rayon fibers began to be disintegrated as a result of decreased bonding ability between the fibers and finally disintegrated into discrete fibers by further continuing the agitaion.

EXAMPLES 4 to 6

The experimental procedure in each of these examples was substantially the same as in Example 3 except that the amount of the fibrous binder added to the water suspension of the rayon fibers was 10, 20 or 90 parts by weight in Examples 4, 5 and 6, respectively, per 100 parts by weight of the rayon fibers. The dispersibility of the staple fibers was satisfactory and rayon paper of good formation could be obtained in each of the examples. The properties of the rayon paper obtained in each example were as shown in Table 1 below.

TABLE 1

|  | Example | | |
|---|---|---|---|
|  | 4 | 5 | 6 |
| Fibrous binder added, parts by weight | 10 | 20 | 90 |
| Properties |  |  |  |
| Basis weight, g/m$^2$ | 85.0 | 73.5 | 66.3 |
| Thickness, mm | 0.287 | 0.259 | 0.060 |
| Density, g/cm$^3$ | 0.297 | 0.284 | 1.104 |
| Breaking length, km | 0.53 | 1.70 | 4.5 |
| Klemm's water absorption, mm/15 seconds | 38 | 34 | — |

The disintegrability of the rayon fibers in water into discrete fibers was complete in each of the examples when the paper was immersed in water and vigorously agitated with a glass rod although the velocity of disintegration was somewhat affected by increasing the amount of the fibrous binder in the water suspension.

EXAMPLES 7 to 11

Fibrous binders were prepared each in substantially the same manner as in Example 1 except that the aqueous dopes for wet-spinning contained sodium alginate and propyleneglycol ester of alginic acid in weight proportions of 95:5, 90:10, 80:20, 70:30 and 60:40 in Examples 7 to 11, respectively, and two platinum-made spinnerettes with holes having diameters of 0.1 mm and 0.055 mm were used.

When the weight proportion of the propyleneglycol ester of alginic acid was increased in the aqueous dope, the fibrous gel after coagulation in the coagulation bath had increased softness and the filament obtained therefrom had a greatly decreased strength although even such a low-strength filament could be wound up continuously on the godet.

Each of the thus prepared five kinds of fibrous binders was cut in a fiber length of 3 mm and the staples were dispersed in water using a standard disintegrator to give a water suspension, of which a paper-making test was undertaken according to the procedure specified in JIS P 8209. In this test, the paper-making screen was overlaid with a cloth of a synthetic fiber of polyvinylidene chloride with an object to facilitate separation of the wet sheet from the screen. The wet sheet on the cloth was dehydrated under a squeezing pressure in the range from 3.5 to 1.0 kg/cm$^2$ followed by air-drying in a conventional manner and the dried sheet was separated by peeling from the cloth to give a sheet of paper composed of the fibrous binder alone. It was clear that the fibers of the fibrous binder had self-adhesiveness suitable for paper making. The properties of the paper obtained in each of these Examples were as shown in Table 2 below.

TABLE 2

|  | Example | | | | |
| --- | --- | --- | --- | --- | --- |
|  | 7 | 8 | 9 | 10 | 11 |
| Sodium alginate: propyleneglycol ester of alginic acid, weight ratio | 95:5 | 90:10 | 80:20 | 70:30 | 60:40 |
| Properties |  |  |  |  |  |
| Basis weight, g/m$^2$ | 73.9 | 54.6 | 81.3 | 92.9 | 97.6 |
| Thickness, mm | 0.107 | 0.084 | 0.089 | 0.079 | 0.083 |
| Density, g/cm$^3$ | 0.674 | 0.647 | 0.914 | 1.18 | 1.17 |
| Breaking length, km, | 1.67 | 2.61 | 2.15 | 4.77 | 4.32 |

What is claimed is:

1. A fibrous binder formed of a water-insoluble gel comprising a water-insoluble metal salt of alginic acid and an alkylene-glycol ester of alginic acid.

2. The fibrous binder as claimed in claim 1 wherein the metal in the water-insoluble metal salt of alginic acid is selected from the group consisting of calcium, barium, strontium, aluminum, zinc, nickel, cobalt, chromium, copper, manganese and lead.

3. The fibrous binder as claimed in claim 2 wherein the metal is calcium.

4. The fibrous binder as claimed in claim 1 wherein the alkyleneglycol is selected from the group consisting of ethyleneglycol, propyleneglycol and butyleneglycol.

5. The fibrous binder as claimed in claim 4 wherein the alkyleneglycol is propyleneglycol.

6. The fibrous binder as claimed in claim 1 wherein the weight proportion of the water-insoluble metal salt of alginic acid and the alkyleneglycol ester of alginic acid is in the range from 95:5 to 10:90.

* * * * *